United States Patent
Debbins et al.

(10) Patent No.: US 7,020,868 B2
(45) Date of Patent: Mar. 28, 2006

(54) GRAPHIC APPLICATION DEVELOPMENT SYSTEM FOR A MEDICAL IMAGING SYSTEM

(75) Inventors: Josef P. Debbins, Waukesha, WI (US); Kristine L. Gould, Delafield, WI (US); Paul E. Licato, Wauwatosa, WI (US); Jason A. Polzin, Lake Mills, WI (US); Deepa Thomas, Waukesha, WI (US); Mark T. Radick, Muskego, WI (US); Giora Sat, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 814 days.

(21) Appl. No.: 09/839,055

(22) Filed: Apr. 20, 2001

(65) Prior Publication Data

US 2002/0060566 A1    May 23, 2002

Related U.S. Application Data

(63) Continuation-in-part of application No. 09/721,233, filed on Nov. 22, 2000, now abandoned.

(51) Int. Cl.
G06F 9/44 (2006.01)

(52) U.S. Cl. .................... 717/108; 717/172; 717/178
(58) Field of Classification Search ............... 717/109, 717/108, 172, 178
See application file for complete search history.

(56) References Cited

U.S. PATENT DOCUMENTS

| | | | | |
|---|---|---|---|---|
| 5,235,510 A * | 8/1993 | Yamada et al. | ............ | 600/300 |
| 5,602,934 A * | 2/1997 | Li et al. | .................... | 382/128 |
| 5,668,998 A * | 9/1997 | Mason et al. | .............. | 717/104 |
| 5,850,548 A * | 12/1998 | Williams | ................... | 717/107 |
| 5,950,002 A * | 9/1999 | Hoford et al. | ............. | 717/109 |
| 5,970,243 A * | 10/1999 | Klein et al. | ................ | 717/113 |
| 6,157,194 A * | 12/2000 | Vassallo et al. | ............ | 324/322 |
| 6,173,438 B1 * | 1/2001 | Kodosky et al. | ........... | 717/109 |
| 6,279,030 B1 * | 8/2001 | Britton et al. | ............. | 709/203 |
| 6,282,699 B1 * | 8/2001 | Zhang et al. | .............. | 717/109 |
| 6,292,827 B1 * | 9/2001 | Raz | .......................... | 709/217 |
| 6,718,533 B1 * | 4/2004 | Schneider et al. | ......... | 717/100 |
| 2002/0029376 A1 * | 3/2002 | Ambrose et al. | .......... | 717/113 |
| 2002/0113590 A1 * | 8/2002 | Haworth et al. | ........... | 324/309 |
| 2003/0039392 A1 * | 2/2003 | Eckstein | .................... | 382/168 |

OTHER PUBLICATIONS

Atkins, M.S., "Role of Visual Languages in Developing Image Analysis Algorithms", Zuk, T., Johnston, B, & Arden, T., p. 262-268, 1994 IEEE [retrieved Jun. 22, 2004].*

(Continued)

*Primary Examiner*—Wei Y. Zhen
*Assistant Examiner*—Mary Steelman
(74) *Attorney, Agent, or Firm*—Ziolkowski Patent Solutions Group, SC; Michael A. Della Penna; Carl B. Horton

(57) ABSTRACT

A workstation is programmed to operate as an application development system for a medical imaging system. Objects programmed in an object-oriented language are selected from a component library using a visual component assembler which enables them to be dragged from a framework area on a display to a workspace area. Properties of selected components may be edited, and the resulting collection of components may be graphically linked together and saved as an application program.

17 Claims, 8 Drawing Sheets

OTHER PUBLICATIONS

"About Coreco—Brief History", release Jun. 18, 2001, 2 pages [retrieved Jun. 22, 2004] Retrieved from the Internet: <URL: http://www.coreco.com/Web/home.nst/0/8467af9ed556f1c185268c100718a8a?OpenDocument&Lang=Gb>.*

National Instruments, "Vision Applications growing for Computer-Based Vision Measurements", 1999, 2 pages [retrieved Jun. 22, 2004] Retrieved from the Internet: <URL: http://www.tinkersguild.com/sample/SponsorAds/Natinstruments/vision_basics.htm>.*

GlobalSpec.com, "WiT 8.0", 1999-2004, 2 pages [retrieved Jun. 22, 2004] Retrieved from the Internet: <URL: http://www.globalspec.com/FeaturedProducts/Detail?ExhibitD=9976>.*

* cited by examiner

GRAPHIC APPLICATION DEVELOPMENT SYSTEM FOR A MEDICAL IMAGING SYSTEM

This is a continuation in part of application Ser. No. 09/721,233, filed Nov. 22, 2000, now abandoned.

BACKGROUND OF THE INVENTION

The field of the invention is medical imaging systems, and particularly, systems for developing software applications for such imaging systems.

There are many types of medical imaging systems. The primary distinction between the different systems is the medical imaging modality that is used, such as, x-ray, magnetic resonance, ultrasound or nuclear. In addition, a broad range of capabilities and features are typically offered in each imaging modality. For example, a magnetic resonance imaging ("MRI")system may be offered with a range of polarizing magnetic strengths and configurations and with a range of different optional features such as magnetic resonance angiography ("MRA"), cardiac imaging and functional magnetic resonance imaging ("fMRI").

Despite the many differences, medical imaging systems have a number of basic functions in common. All medical imaging systems include an operator interface which enables a particular image acquisition to be prescribed, a data acquisition apparatus which uses one of the imaging modalities to acquire data from the subject, an image reconstruction processor for reconstructing an image using acquired data, and storage apparatus for storing images and associated patient information. Typically, hardware is designed to carry out these functions and system software is designed and written for each hardware configuration.

A medical imaging system contains application programs which direct the imaging system to perform particular types of scans, image reconstructions and post processing applications. For example, an MRI system may include application software which directs the imaging system to perform a fast spin-echo scan, or a fast gradient-recalled echo scan, or a functional MRI scan, or a cardiac cine scan. The application software also directs the imaging system to reconstruct images from acquired data. Typically, a medical imaging system will include software programs to reconstruct one or more images from a set of acquired data, wherein the algorithms are designed to process the acquired data differently to reconstruct, for example, either stationary skeletal or tissue images, or images of blood flow through a body.

Each of these different applications requires the writing of software code in a language such as assembler, or C and the linking and compiling of such code for use in the MRI system. As the number of applications grows, the amount and complexity of the application software code becomes increasingly difficult to maintain. As a result, the addition of new applications to the imaging system becomes increasingly difficult. Furthermore, because of the difficulty of writing and compiling application software, it is extremely difficult for users of medical imaging systems to experiment with new methods of scanning and particularly, of reconstructing data. To modify the scan and reconstruction procedures, trained programmers and a significant degree of down time of the machine can be required.

SUMMARY OF THE INVENTION

The present invention is an application development system for a medical imaging system, and particularly, a system for producing an object oriented application program from a library of stored components, each component containing methods in the form of executable code and data related to the operation of the medical imaging system. The application development system includes a memory for storing a library of components; a display containing a framework area providing an indication of the components stored in the library, containing a workspace area for indicating components selected from the library to form an application program, and containing a properties area for indicating instance variables of a selected component; an input device; and a processor programmed to enable a user to select with the input device components indicated in the framework area and place them in the workspace area, programmed to edit with the input device instance variables indicated in the properties area for a selected component, and programmed to store the components in the workspace area as an application program.

Application programs may be created without writing and compiling program code. All program code is contained in the components stored in the library and the selection of components and placement in the workspace area of the display links the program code and any modified properties, or instance variables into a single application program which can be "persisted". The application program is stored on the medical imaging system along side the component library, and when the application is selected to perform a scan, the program code from the proper components in the component library are linked together per the design of the stored application, and their instance variables set as indicated by the application program. The program code is preferably written in a transportable object oriented programming language, such that data processing components can be easily developed on a first computer system or cpu and downloaded to a second system. Therefore, developed applications can be easily shared among medical practitioners and among medical facilities. Applications can also be developed at an external, off-line computer, thereby allowing for the development of applications without the need to tie up expensive scanning equipment.

Preferably, the application development system comprises a series of predefined, executable code segments with defined input and output links. The executable code segments can be dragged and dropped onto a graphic building area, and linked together graphically through the connection points to provide application code, which is serialized and downloaded to application specific processors for execution. The graphic building area comprises a plurality of icons which can be easily linked together with a mouse or other input device, thereby making construction and compilation of an imaging application or a specific segment of an imaging application very easy.

In addition to providing a simple and easy way to program applications, the graphical building area is particularly suited to the development and manipulation of image reconstruction pipelines. Data processing steps for image reconstruction can be graphically modified in real time to modify or improve both collected and visualized data. During real-time processing of an image, the user can modify various parameters, including filtering and threshold parameters, dynamic range and sampling parameters, image resolution, and data flow control in and out of a reconstruction processing pipeline. After a modification has been made, an indication of a change of process and the programming code for processing the acquired data is serialized and downloaded to a data processing board. The data processing board and/or an associated processor preferably translates the programming code to a low level language such as C or assembly which can operate at an appropriate speed to process real-time data. During real-time data acquisition and processing, therefore, a number of data processing parameters and reconstruction parameters can be modified and forwarded to the processing board to modify or improve data imaging and reconstruction.

GENERAL DESCRIPTION OF THE INVENTION

Figure 5:
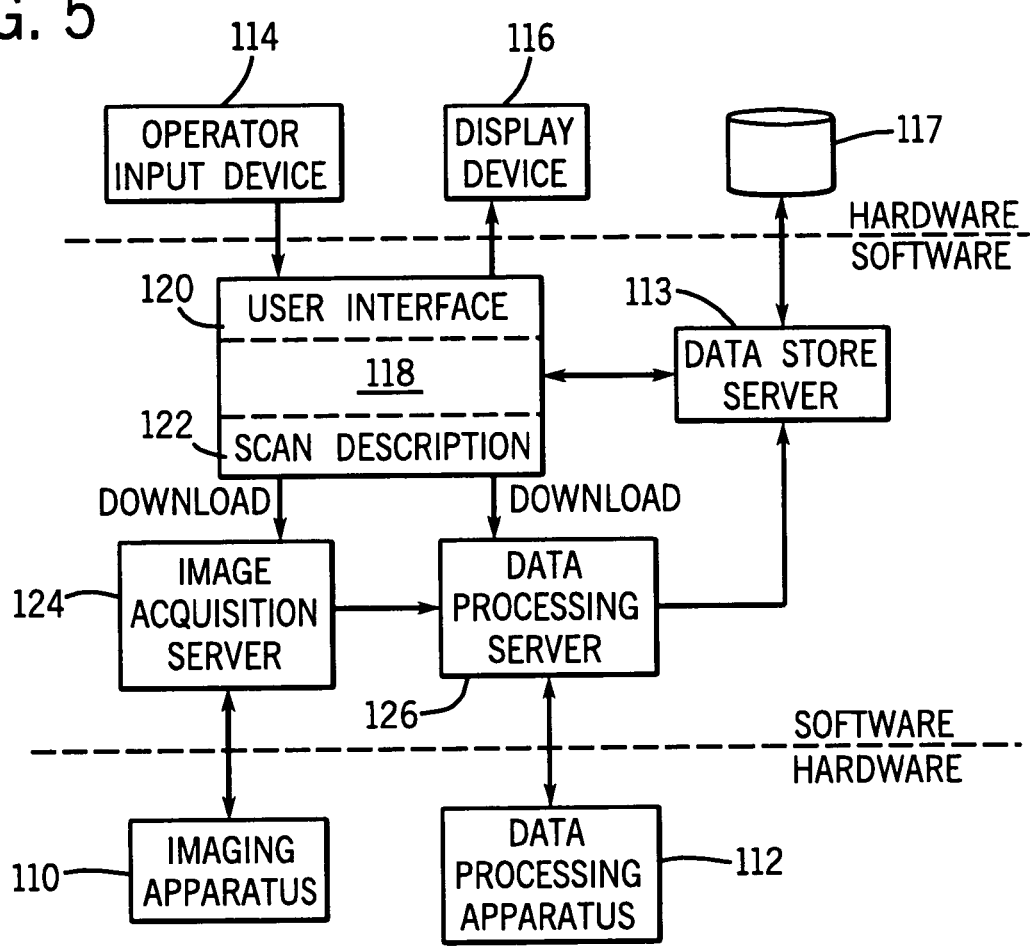
FIG. 5 is a block diagram of an imaging system which employs the present invention.

Referring particularly to FIG. 5, a medical imaging system includes imaging apparatus 110 comprised of mechanical and electrical hardware elements that are operated during a scan to acquire image data. The imaging system also includes data processing apparatus 112 that is operated to reconstruct images using the acquired image data. To operate the system and to enter a scan prescription an operator input device 114, such as a keyboard and control panel, is provided, a display device 116 is provided to present the images for visualization and a storage device 117, such as a hard disc drive, is provided to archive acquired images. The particular imaging modality used, and the complexity and power of these hardware elements varies substantially from one system to the next.

The system includes a workstation 118 which is programmed in a machine independent language, such as Java™, to provide a user interface 120 that enables an operator to enter scan parameters using the operator input device 114. The workstation 118 is programmed to produce a scan description 122, which in its simplest configuration contains image acquisition description components and data processing description components that contain information required by the imaging apparatus 110 and data processing apparatus 112 to perform the prescribed scan.

Prior to run time, a snap shot of the scan description 122 is downloaded to a plurality of servers which control the imaging system hardware apparatus. In the simplest configuration these include an image acquisition server 124 and a data processing server 126 which operate the respective imaging apparatus 110 and data processing apparatus 112. When provided with the scan description components, the servers' programs direct the image system hardware apparatus to perform the prescribed scan. A data store server 113 directs the storage device 117 to save the images along with associated patient information.

The particular scan or operation that is performed by the medical imaging system is directed by an application program stored in the workstation 118.

The application program is produced using an application development system that runs on the workstation 118 or a separate workstation (not shown). The application development system enables the user to create a new application program by selecting objects, or components, written in an object-oriented programming language, from a component library, and assemble them using a visual component assembler. The instance variables of selected components are displayed and may be edited for the new application program. The assembled components are instantiated and saved as a new application program which may be reconstituted for use on the medical imaging system. Instantiation is achieved using a serialization process in which the hierarchical relationship of components and their instance variables are stored.

DESCRIPTION OF THE PREFERRED EMBODIMENT

Figure 1:
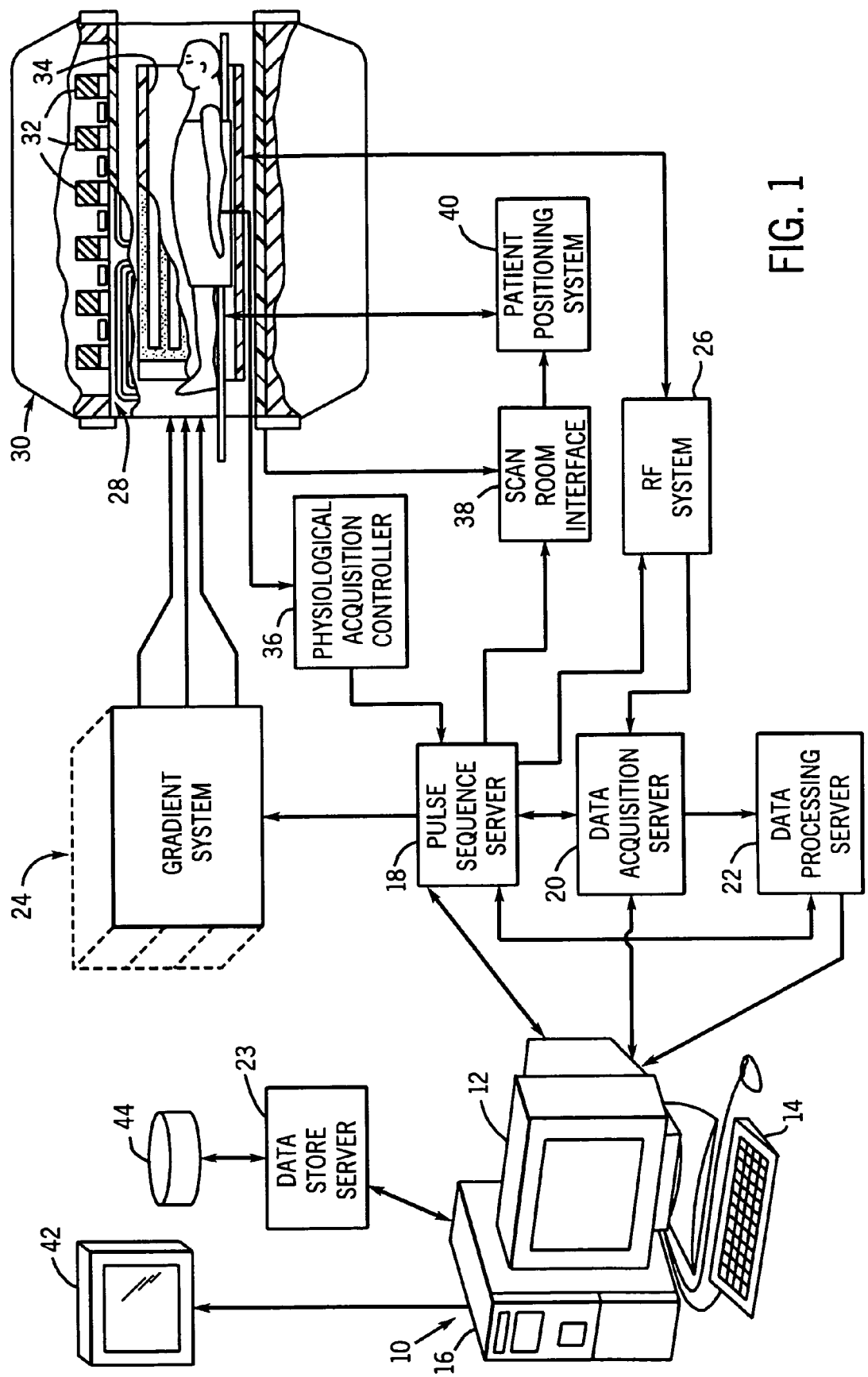
FIG. 1 is a block diagram of an MRI system which employs the preferred embodiment of the invention.

Referring particularly to FIG. 1, the preferred embodiment of the invention is employed to operate an MRI system. The MRI system includes a workstation 10 having a display 12 and a keyboard 14. The workstation 10 includes a processor 16 which is a programmable machine commercially available from Silicon Graphics, Inc. It is based on a 64-bit microprocessor manufactured by Intel and it runs the Linux operating system. The workstation 10 provides the operator interface which enables scan prescriptions to be entered into the MRI system. As will be described in more detail below, the workstation 10 will run one or more Java™ virtual machines which will run code which is programmed in the Java™ language that is fully transportable to any other programmable machine which is Java™ compatible.

The workstation 10 is coupled to four servers: a pulse sequence server 18; a data acquisition server 20; a data processing server 22, and a data store server 23. In the preferred embodiment the data store server 23 is performed by the workstation processor 16 and associated disc drive interface circuitry. The remaining three servers 18, 20 and 22 are performed by separate processors mounted in a single enclosure and interconnected using a 64-bit backplane bus structure based on the PCI standard for industrial and telecommunications applications called "CompactPCI". The pulse sequence server 18 employs a 366 MHz microprocessor model PPC750 and a quad communication controller model MPC860T manufactured by Motorola, Inc. The data acquisition server 20 and data processing server 22 both employ the same 366 MHz microprocessor and the data processing server 22 further includes one or more array processors based on parallel vector processors commercially available from Mercury Computer Systems, Inc. as the PowerPC™. Another 366 MHz microprocessor (not shown) serves as a hardware controller on the PCI bus structure and it controls a quad communication controller model MPC860T manufactured by Motorola, Inc.

The workstation 10 and each processor for the servers 18, 20 and 22 are connected to a 100 BaseT Ethernet serial communications network. This serial network conveys data that is downloaded to the servers 18, 20 and 22 from the workstation 10 and it conveys tag data that is communicated between the servers and between the workstation and the servers. In addition, a high speed data link using the BIT3 protocol is provided between the data processing server 22 and the workstation 10 in order to convey image data to the data store server 23.

The pulse sequence server 18 functions in response to program elements downloaded from the workstation 10 to operate a gradient system 24 and an RF system 26. Gradient waveforms necessary to perform the prescribed scan are produced and applied to the gradient system 24 which excites gradient coils in an assembly 28 to produce the magnetic field gradients $G_x$, $G_y$ and $G_z$ used for position encoding NMR signals. The gradient coil assembly 28 forms part of a magnet assembly 30 which includes a polarizing magnet 32 and a whole-body RF coil 34.

RF excitation waveforms are applied to the RF coil 34 by the RF system 26 to perform the prescribed magnetic resonance sequence. Responsive NMR signals detected by the RF coil 34 are received by the RF system 26, amplified, demodulated, filtered and digitized under direction of commands produced by the pulse sequence server 18. Exemplary RF systems are described in U.S. Pat. No. 4,952,877 and U.S. Pat. No. 4,992,736.

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize the performance of the scan.

The pulse sequence server 18 also connects to a scan room interface circuit 38 which receives signals from various sensors associated with the condition of the patient and the magnet system. It is also through the scan room interface circuit 38 that a patient positioning system 40 receives commands to move the patient to desired positions during the scan.

It should be apparent that the pulse sequence server 18 performs real-time control of MRI system elements during a scan. As a result, it is necessary that its hardware elements be operated with program instructions that are executed in a timely manner. As will be explained in more detail below, the pulse sequence server 18 is controlled during run-time by programs written in a low level programming language such as assembler, C or C++. The description components for a scan prescription are downloaded from the workstation 10 in the form of objects. The pulse sequence server 18 contains programs which receive these objects using a serialization mechanism. The pulse sequence server 18 also includes a program which converts the objects to C++ objects that are employed by the run-time programs. In the preferred embodiment Java™ objects are downloaded and the Java™ serialization mechanism is employed. The pulse sequence server 18 thus includes both hardware independent programs written in Java™ and hardware dependent programs. It is contemplated that Java™ interpreters will eventually become fast enough that nearly all programs run on the pulse sequence server 18 will be written in hardware independent form.

The digitized NMR signal samples produced by the RF system 26 are received by the data acquisition server 20. The data acquisition server 20 operates in response to description components downloaded from the workstation 10 to receive the real-time NMR data and provide buffer storage such that no data is lost by data overrun. In some scans the data acquisition server 20 does little more than pass the acquired NMR data to the data processor server 22. However, in scans which require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Navigator signals may be acquired during a scan and used to adjust RF or gradient system operating parameters or to control the view order in which k-space is sampled. And, the data acquisition server 20 may be employed to process NMR signals used to detect the arrival of contrast agent in an MRA scan as described in co-pending U.S. pat. appln. Ser. No. 08/635,078 filed Apr. 19, 1996 and entitled "*Method For Performing Magnetic Resonance Angiography Using a Contrast Agent*". In all these examples the data acquisition server 20 acquires NMR data and processes it in real-time to produce information which is used to control the scan.

As with the pulse sequence server 18, the hardware elements of the data acquisition server 20 are operated at run-time with program instructions in a programming language such as assembler, C or C++. As will be explained in more detail below, the directions for its operation during a scan are downloaded from the workstation 10 in the form of objects. A server proxy receives the objects using the serialization mechanism and the downloaded objects are converted to C++ objects that are employed to operate the data acquisition server 20 during run-time. As indicated above, Java™ objects are downloaded in the preferred embodiment using the Java™ serialization mechanism.

The data processing server 22 receives NMR data from the data acquisition server 20 and processes it in accordance with description components downloaded from the workstation 10. Such processing may include, for example: Fourier transformation of raw k-space NMR data to produce two or three-dimensional images; the application of filters to a reconstructed image; the performance of a backprojection image reconstruction of acquired NMR data; the calculation of functional MR images; the calculation of motion or flow images, etc.

Images reconstructed by the data processing server 22 are conveyed back to the workstation 10 where they are stored. Real-time images are stored in a data base memory cache (not shown) from which they may be output to operator display 12 or a display 42 which is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Directions for the particular operations to be performed by the data processing server 22 are downloaded from the workstation 10. The time critical functions are performed with programs written in assembler, C or C++ and the downloaded Java™ object directions must be converted to corresponding executable code as described above.

Figure 2:
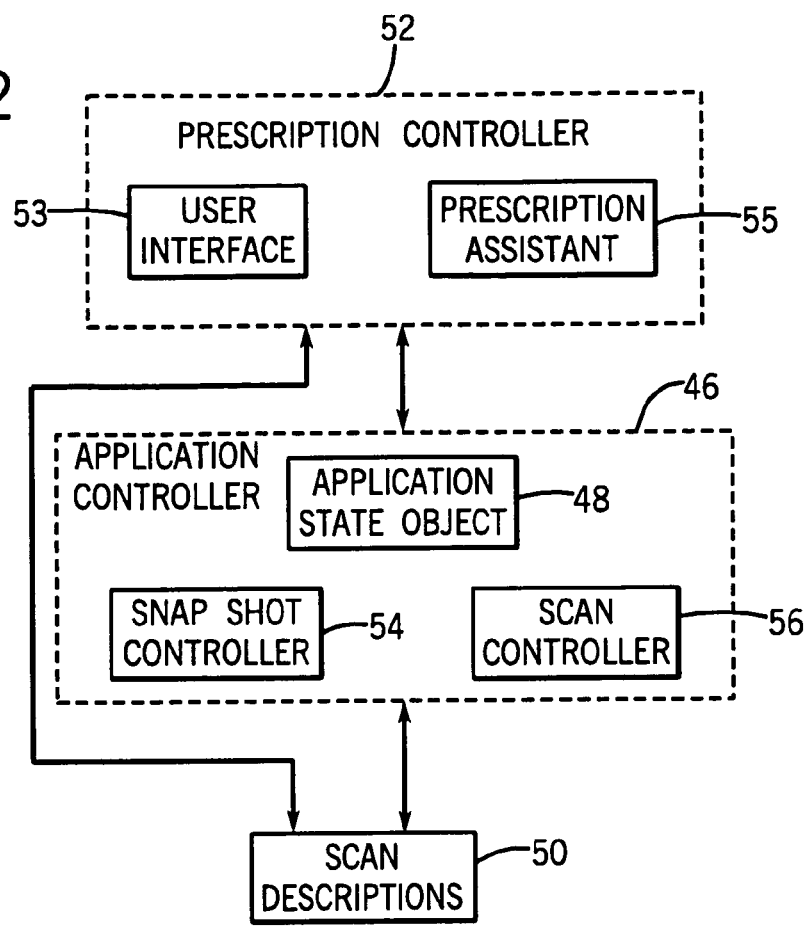
FIG. 2 is a block diagram of functional components in a workstation which forms part of the MRI system of FIG. 1.

As indicated above, the workstation 10 is a Java™ virtual machine which executes programs written in the Java™ programming language. The workstation software is structured to perform "applications" which may be selected and run by an operator. Such applications correspond to clinical imaging procedures and may include, for example:

perform a scan using an FSE pulse sequence;
conduct a CEMRA dynamic study;
perform an fMRI study;
perform a runoff vascular study
perform image post processing
filming
networking An application is a collection of Java™ objects stored in an "application container" that may be selected by an operator to perform a scan. Referring particularly to FIG. 2, each application container includes a Java™ application controller component 46 which directs other Java™ components in the container to perform the scan. These other components include a prescription controller 52 which includes a user interface component 53 and a prescription assistant component 55 that enable an operator to control the procedure performed by the application.

The application container also includes scan descriptions 50. These scan descriptions are downloaded to the servers 18, 20, 22 and 23 (FIG. 1) and used by those servers to perform the prescribed scan. The stored scan descriptions 50 are unique for every different application.

The preferred embodiment of the present invention is an application development system which produces application programs for this MRI system. This application program is a collection of interrelated Java™ objects within the application container Java™ object. These objects are selected and edited using tools in the application development system. The application development system may reside on the MRI system workstation 10, or it may reside on a separate, stand alone workstation of similar structure and capability.

After the application program is developed, the application container object is serialized and stored in the disc storage 44. When the operator of the MRI system selects the application program, the corresponding serialized application container object is read from the disc memory 44 and reconstituted as shown in FIG. 2 to operate the MRI system. To better understand the requirements of the application development system, the operations performed by the MRI system under the direction of the application program will now be described.

The application controller 46 includes an application state object 48 which maintains the state of the application as the scan is performed. The possible states during a life cycle of an application are as follows:
Initialization
Prescribing
Prescribed
Downloading
Downloaded
Prescanning
Prescanned
Batch Scanning
Real Time Scanning
Scan Paused
Scanned
Reconstructed
Visualized.

This life cycle is driven by commands from the application container (like initialize application), by commands from the operator (like start scan) and by commands generated internally by the application (like scan done).

When the operator initially selects the application, the application initializes and changes to the "prescribing state" and the prescription controller 52 is enabled to interact with the scan description components 50 to determine what scan parameters must be specified by the operator (e.g. TR, number of slices, location of FOV, flip angle) and determine if the prescription is complete and valid. The prescription controller 52 then signals the application state object 48 to switch to the "prescribed" state and download, prescan and scan buttons on the control panel are enabled.

If the operator hits the "download" button, the application state object 48 changes to the "download state" and the application controller 46 employs a snap shot controller 54 to issue snap shot and download commands. As will be described in more detail below, these commands cause the scan descriptions 50 to be downloaded to the servers 18, 20, 22 and 23. The snap shot controller 54 receives "download done" notification back from each of the servers 18, 20, 22 and 23, and when all four servers have been downloaded, the application state object 48 is changed to the "downloaded" state.

If the operator hits the scan button, the application state object 48 will change to the scan mode and a scan controller 56 is employed to issue a scan command to the pulse sequence server 18. The next state transition is governed by the scanning mode i.e., real-time or batch. The behavior of the application in the two modes is very different and so there are two different scanning states. If in real-time mode, the application is set to a "real-time scanning" state and if in batch mode, the application state is set to a "batch scanning" state. When in the real-time mode, if the user chooses to pause the scan, the application will transition to a "scan paused" state. If scanning is resumed, the application goes back to the real-time scanning state. In real-time scanning state, the application can be edited and edited descriptions will be downloaded even while the scanning is in progress. However, the application will not make a state transition; instead, the same state will be characterized to allow editing and downloading. It is this behavior of the real-time scanning state that differentiates it from the batch scanning state.

The application will make a transition to the "scanned" state when the operator hits the "stop scan" button. Also, if the application is in the batch scanning mode of operation, the pulse sequence server 18 notifies the application controller 46 when the scan is completed. The application state object changes to the "scanned" state in either event.

When the data processing server 22 completes reconstruction of the acquired images, the application controller 46 is notified and the application state object 48 is changed to the "reconstructed" state. This indicates to the workstation 10 that reconstructed images are available on disk 44 for display or further processing.

The scan descriptions 50 contain a set of components that serve to collect scan parameters using the prescription controller 52, and to organize those prescription scan parameters into a set of smaller components that can be downloaded to the servers 18, 20, 22 and 23. On the servers 18, 20, 22 and 23, those downloaded components direct the operation of the hardware in order to carry out the prescribed scan.

There are different description types within each application to provide logical groupings of components to deal with different aspects of executing an MR scan. These description types are:
Pulse Description;
Sequence Description;
Acquisition Description;
Data Processing Description;
Data Store Description.

The pulse description includes components that define and control the waveforms to be played out on the gradient system and the RF system hardware, along with hardware control components. These components control the dynamic aspects of the waveforms and hardware in response to events produced at run-time by components of the sequence description. This description also includes components that control the filtering of NMR signals received by the RF system 26. These components collectively define a unique set of gradient/RF/control pulses which are used to excite, encode, and readout the NMR signals. Examples are pulse descriptions for 2D spin echo, 2D gradient-echo, 2D fast spin-echo, and 3D gradient-echo sequences.

The sequence description includes a set of components that control the order of pulse sequences played out, and define a series of prescribed events along the scan timeline. These prescribed events defined by the sequence description trigger the dynamic behavior of the pulse components in the pulse description. These components prescribe a unique acquisition ordering used to define the slice and k-space sampling order. Examples are 2D sequential, 2D interleaved, 3D sequential, 3D elliptical centric, and multi-slice CINE.

The acquisition description includes a set of components that prescribe the real-time processing of NMR signals acquired by the RF system 26. These components direct the performance of operations on acquired NMR signals to produce information that is fed back to components in the sequence description to affect subsequent scanner operation. These components may, for example, process NMR signals during a calibration prescan to feedback changes in the power or frequency of RF pulses produced during the subsequent scan; or process NMR signals to detect when a bolus of contrast agent arrives in a region of interest and trigger the start of a centric view order acquisition; or process "navigator" NMR signals to produce phase correction information which may be used to alter the view order of the scan or alter the demodulation reference frequency of the RF system 26. There are scans commonly used in clinical applications which do not require this capability, however, and in those applications, the components in the acquisition description simply buffer or filter the acquired NMR signals and make them available to the data processing server 22.

The data processing description contains components that direct the data processing server 22 to transform acquired NMR signals into a meaningful form. Spectroscopy processing can be defined by these components, in which case the form that results is an image of the spectra of the acquired NMR signals. Image reconstruction is, however, the most common function and the resulting form is a 2D or 3D image of the subject being scanned. Image reconstruction components can include image manipulation functions such as rotating and transposing images; various types of transformation functions including fourier transforms; data sampling, windowing, and filtering functions; sorting and directing collected and manipulated data between a number of possible data manipulation applications, and other applications. Properties of these components can also be modified during scanning to modify the stored and visualized images, as discussed more fully below. Certain components can also be modifed during processing of an acquired image, either during operation of a scan or during off-line image processing. These components can include, for example: data filter parameters, threshold values, image resolution values, the control of pipeline parameters directed to data processing, and other data processing parameters.

The data store description contains components that define the images which are stored in the database during a scan. In addition to the reconstructed images, this may include patient information and scan parameter information which is to appear annotated on the image along with the patient anatomic or spectrographic information.

Figure 3:
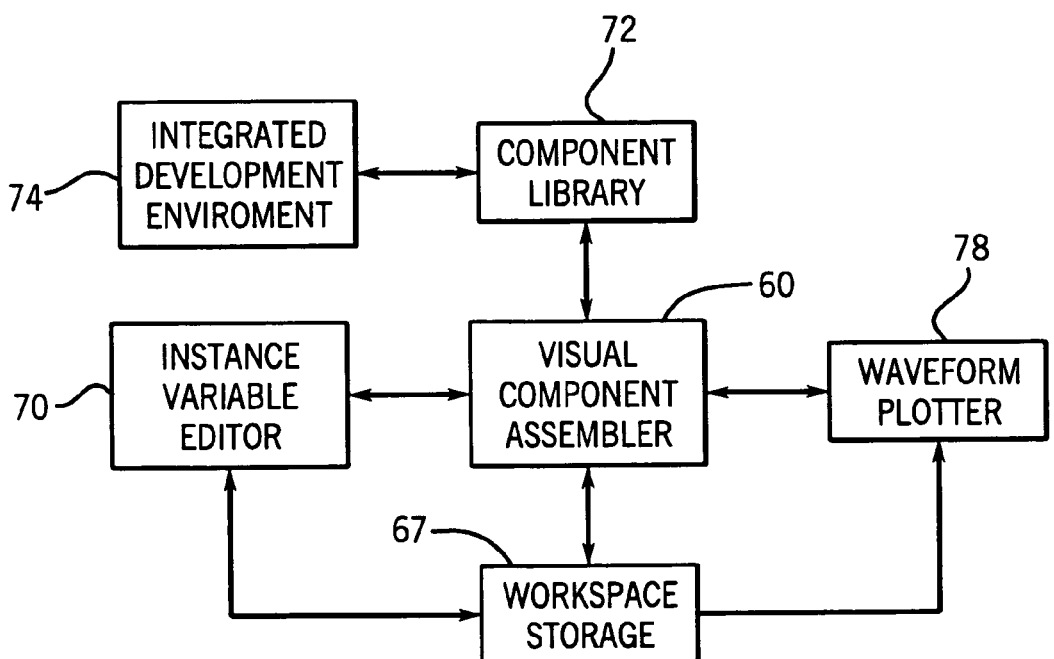
FIG. 3 is a block diagram of the software architecture of a preferred embodiment of an application development system which employs the present invention.
Figure 4:
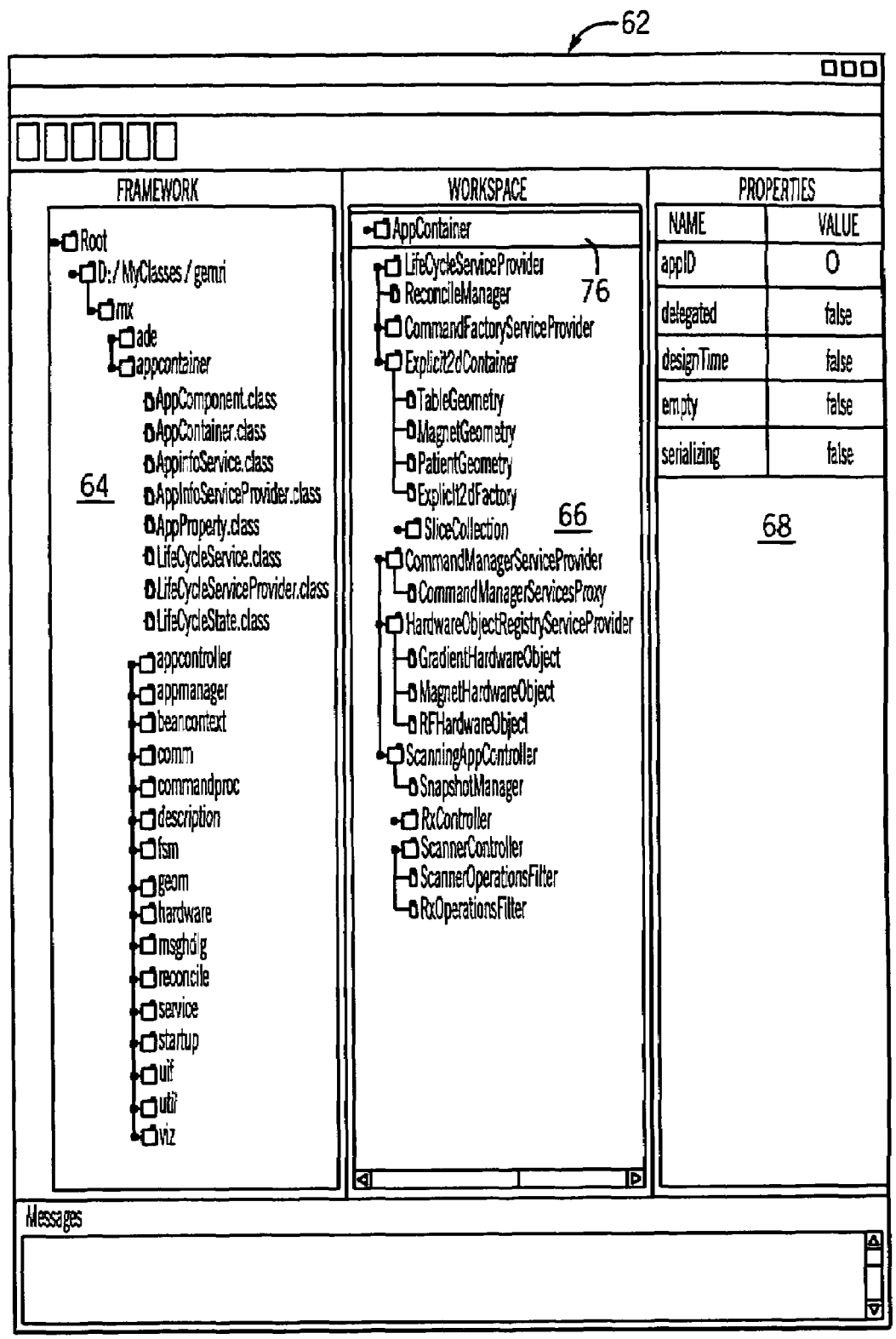
FIG. 4 is a pictorial representation of a display produced by a visual component assembler which forms part of the software architecture of FIG. 3.

As indicated above, the application development system is implemented on a workstation having a memory, a display, an input device such as a keyboard and mouse and a processor programmed to perform the functions now to be described. Referring particularly to FIGS. 3 and 4, the programs and data which form the software architecture of the application development system includes a visual component assembler 60 which produces a window display 62 to the user that contains three areas: a framework area 64; a workspace area 66; and a properties area 68. The application program is developed by selecting components from the component library 72 which are displayed in the framework area 64 and dragging them into the workspace area 66. Such selected components are stored in workspace storage 67. The properties of a selected component in the workspace area 66 are displayed in the properties area 66, and these properties can be changed using an property editor 70.

The components displayed in the framework area 64 are Java™ classes, or objects stored in a component library 72. These components are typically developed using a commercially available integrated development environment 74 such as that sold under the trademark "Forte for Java" by Sun Microsystems or "JBuilder" sold by Inprise. The components are written in Java™ source code and compiled into binary instructions called byte code. These byte code components are saved to the appropriate packages in the component library 72. It can be appreciated that many Java components are commercially available and these can be used along with custom written Java components to create more complex components specifically applicable to performing the MRI functions described above. The objective is to create and store enough components in the component library 72 such that a user can build any desired application by selecting existing components. In such case, the user does not need to write any software code to implement new applications, but is simply requested to select and aggregate the desired functionality.

Figure 6:
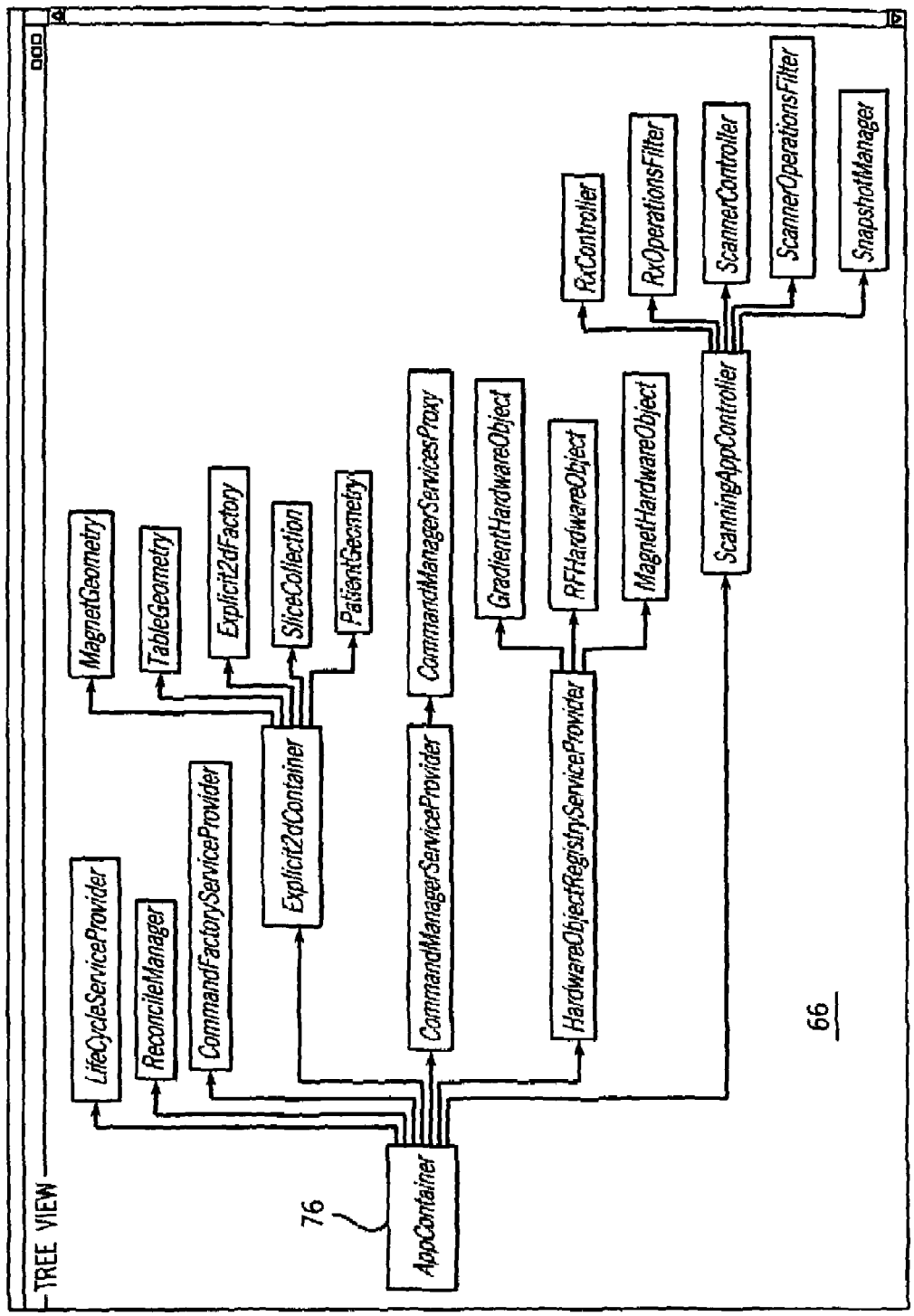
FIG. 6 is a pictorial display of an alternative embodiment of a workspace region in the display of FIG. 4.

Referring particularly to FIGS. 3, 4 and 6, as components are dragged into the workspace 66 from the framework area 64, the visual component assembler 60 establishes the hierarchical relationship between the components. These relationships are illustrated in one preferred manner in FIG. 4 by the indentation of containee component icons beneath their related container component icon. An alternative embodiment of the display of this hierarchical relationship of components in the workspace 66 is shown in FIG. 6. In this embodiment, arrows point from each superclass component icon to its related subclass component icons.

It can be appreciated that the display of a complete application requires more display area than is available and that scroll bars may be used to display different portions of the application in the workspace 66.

To build an application, the user first loads the framework area 64 with the library of components. The components are displayed and an application container component 76 is selected. When this component 76 is dragged to the workspace 66, components for all of its children are also identified. This initiates the building of an application, but the user must know what further components are required to complete the build. To assist in this effort any component in the workspace 66 can be selected with a right click of the mouse and a description of the function performed by that component is displayed in the format known as Javadoc™.

Each component in the workspace 66 has properties, which include numeric variables, Boolean variables and other class type or named variables. The visual component assembler enables the user to display these properties in the properties area 68 by left clicking on a selected component. If the user then left clicks to select one of the displayed properties in the properties area 66, the property editor tool 70 is employed to enable the user to make the change. It is contemplated that most of the new applications created in clinical settings will be limited to changing the properties in components of existing applications. In other words, existing applications are dragged from the framework area 64; the properties in selected components therein are edited; and the result is saved back to the component library 72 as a new application.

When the application is completed the selected components assembled in the workspace area 66 are then persisted. This is currently accomplished by storing the application using the above described serialization mechanism, however, other persistence mechanisms are known and may be used. The persistence mechanism stores the hierarchical relationship ("graph") between the selected components as well as the instance variable (property) values. The byte code for each component in the application is not stored with the persisted application. The medical imaging system which employs the application must itself store the byte code for all the components used in applications. When the persisted application is restored, or "deserialized", on the MRI system, it directs the loading of the byte code indicated by the persisted object graph and instance variable.

Figure 7:
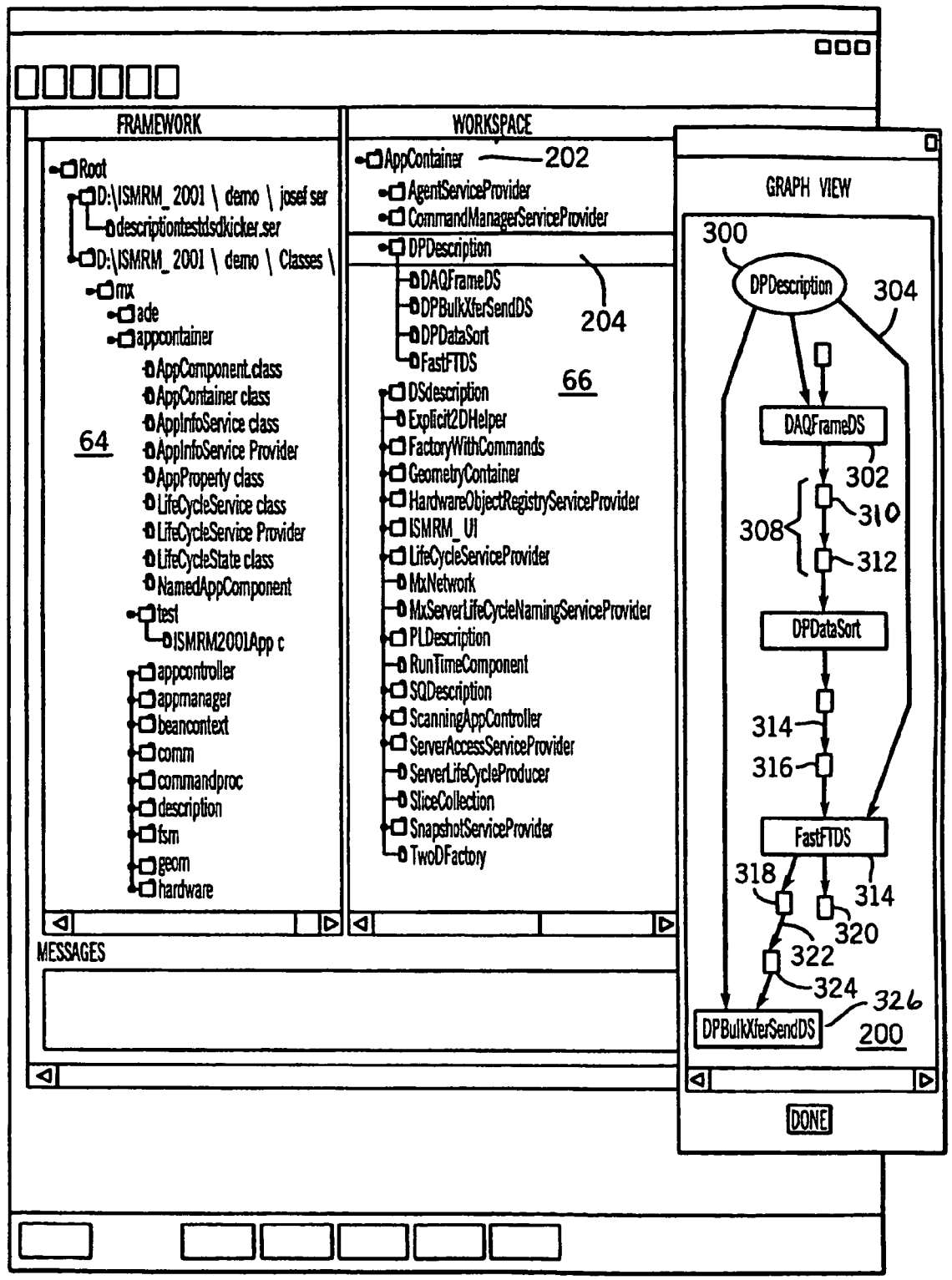
FIG. 7 is a pictorial display of a preferred embodiment of a framework, workspace region and graphic building area in the display of FIG. 4.

Referring now to FIG. 7, a preferred embodiment of the invention wherein the application development environment includes a framework area 64 and workspace 66 in combination with a graphical building area 200 is shown. The workspace 66 includes a main application container 202, and hierarchically arranged beneath the main folder, a plurality of application description folders. Among the folder structures is a data processing description 204, including a plurality of component folders of executable code for providing various data processing functions. The data processing description 204 will be used by way of example for explaining the graphic building area 200 below. However, it will be apparent that the graphic building method described can be applied to a number of different medical imaging applications, either for performing discrete segments such as scan pulses, or for providing an overall imaging acquisition and reconstruction program.

Referring now to the graphical building area 200 of FIG. 7, three basic types of icons are displayed. These include: containers 300, components 302, and connection points 304. The containers 300, which are structural elements which provide a storage location for a number of executable components 302, are represented as oblongs. The executable components 302 are represented as rectangular icons. Each of the components 302 receives and/or transmits data and therefore includes one or more connection point 308 which can be an input 310 and/or output 312. The inputs 310 and outputs 312 can receive or provide signals in the form of events or data. Generally, the connection point 308 is tied to related data through a code representation such as an address.

Properties of each of the containers 300 and components 302 can be accessed by right clicking on the respective icon with a mouse, thereby accessing the properties of the object allowing the user to edit the properties through an input device 14 (FIG. 1). Properties of the connection point 308 are accessed by dragging a mouse over the icon and activating a tip point or other graphical means of display. Information displayed can include a name of the connection point 308 and the type of data expected at or transmitted from.

To build an application or an application segment such as the data processing segment shown, a container 300 is initially dragged and dropped onto the graphic building area 200 with an input device such as a mouse. The container 300 can be an empty object to which components 302 are added from the workspace 66, or a container 300 such as the data processing description 204 shown, which already contains a plurality of components 302. When a container 300 which includes components 302 is dropped onto the graphic building area 200, the relationship between the container 300 and the components 302 is shown graphically with a plurality of graphic links 304. Other components 302 can be selected from the framework 64 or workspace 66 areas and dropped onto the container 300 to add these components to the container. When components 302 are added in this way, graphical links 304 between the container 300 and the added components 302 are also shown.

As each component 302 is dropped onto the graphic building area 200, connection points 308 illustrating input 310 and output 312 connections for transmitting data or events to and from the component 302 are shown as icons. A predetermined number of input 310 and output 312 connection points 308 are associated with each component 302. Using a mouse, keyboard, or other input device 14 (FIG. 1), the user graphically links successive inputs 310 and outputs 312 by means of a graphical assembly link 314 to provide a data flow through the executable code. The graphical assembly link 314 provides each of the connected components with software references to one another, and thus provides a hierarchical linking of the components 302.

After the components 302 are linked, the code can be serialized and downloaded, as described above, either by linking a specialized download component to the assembled code, or by selecting a download button from the user interface 14 (FIG. 1) of the primary application.

The graphical workspace of FIG. 7 is particularly useful in manipulating a data processing pipeline, allowing users to modify the flow and processing of data graphically in both development and real-time processing operations. As an example, FIG. 7 illustrates a data processing container 302 including a fast Fourier transform component 314. The fast Fourier transform component 314 receives one input signal 316 and provides two output signals 318 and 320, respectively. The input 316 to the Fourier transform is preferably a data stream of acquired image data. The output 318 can comprise an array of magnitude data, while the output 320 comprises an array of phase data, each providing a separate set of information about the acquired image, both of which are useful in processing image data. As shown, a graphic assembly link 322 couples the output 318 to an input 324 to a bulk transfer process 326, which transfers the data for further processing. During a processing application, however, it may be desirable to process the phase data of output 320. To change the processing, the user employs an input device such as a mouse to move the graphic assembly link 322 from the output 318 to the output 320.

By including a specialized program component 302 designed to download an application segment such as the data processing segment shown, the revised application can be downloaded to the data processing server as a separate component, without the need to download an entire image processing application. The workstation 118 downloads the revised code, in this case to the data processing server 126 and data processing apparatus 112 which, in turn, modifies the data flow to provide the phase data represented as output 320 to the bulk transfer process.

Figure 8:
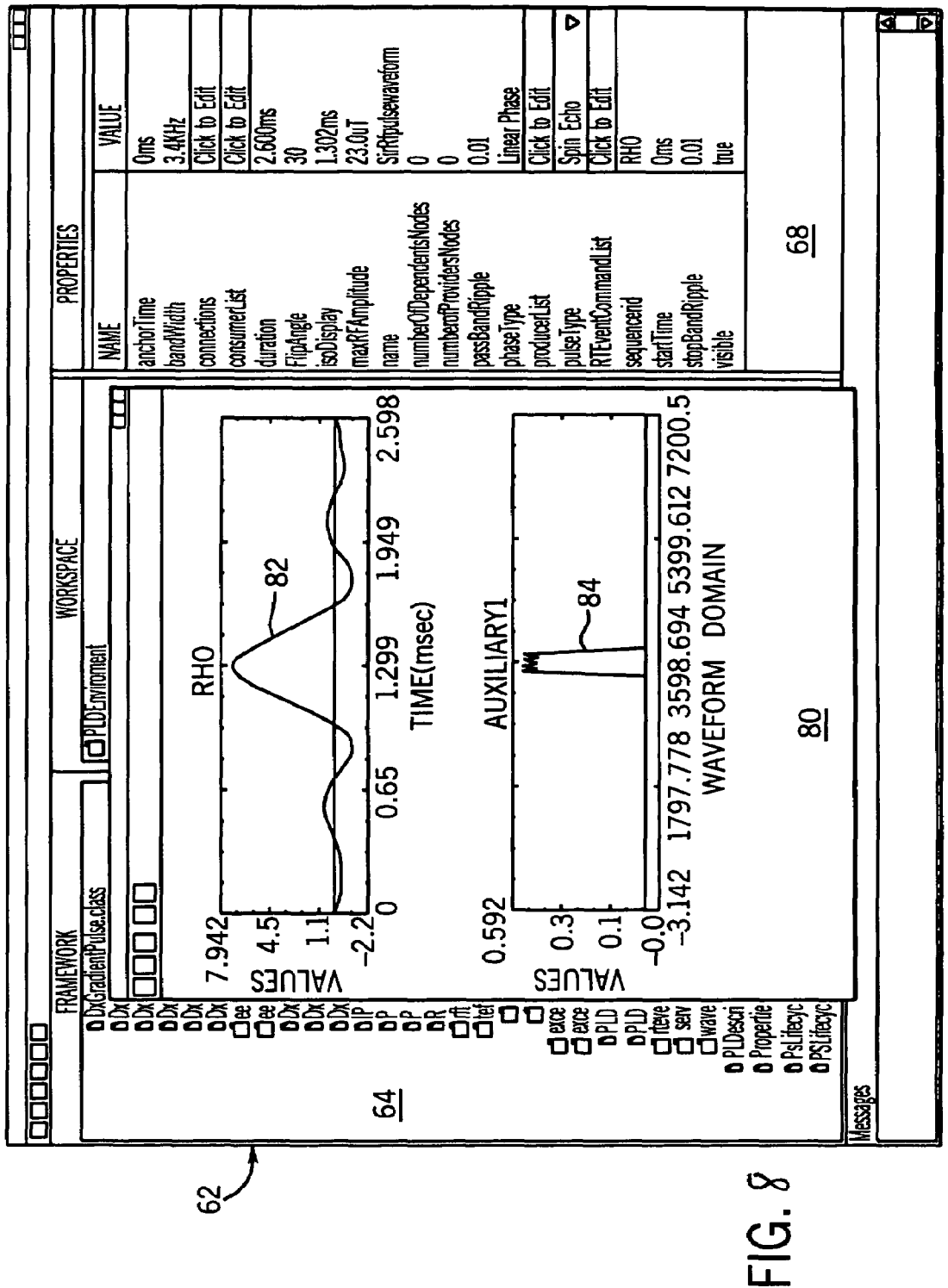
FIG. 8 is a pictorial display of a properties portion of the display in FIG. 4 depicting an rf pulse component.
Figure 9:
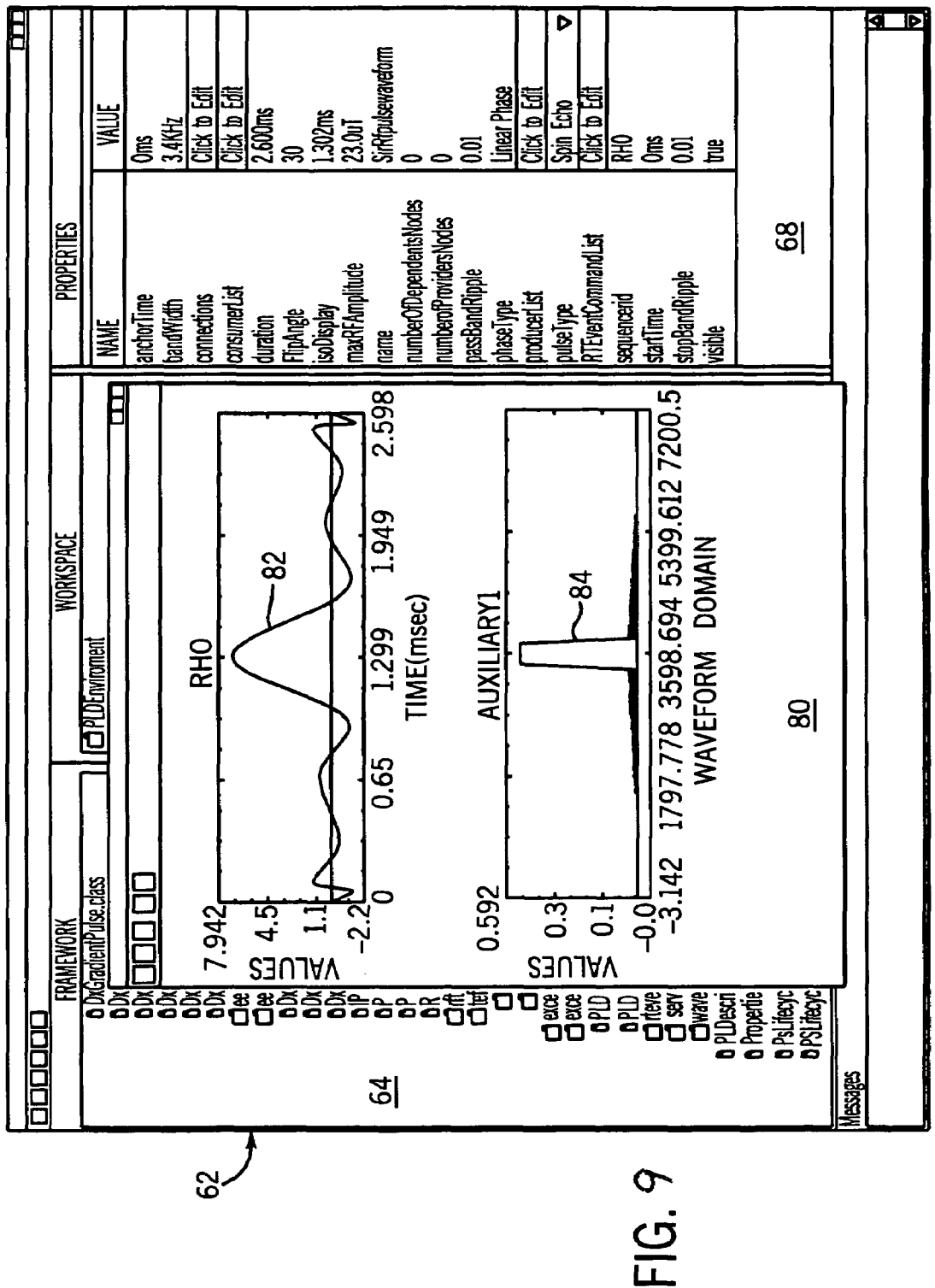
FIG. 9 is a pictorial display showing a graphic plot of the rf pulse component of FIG. 8.

Because many of the components in MRI applications relate to the production of pulses and pulse sequences, another feature of the present invention is the display of waveforms or other data produced by a component. Referring particularly to FIGS. 3, 8 and 9, all components, may include a property called a "visible." In the case of a pulse waveform component, when the visible property is switched to "true", a waveform plotter 78 is enabled and a pulse sequence plotter window 80 is produced and displayed. This window 80 displays the waveforms 82 and 84 which are produced by this instance of the component. If a property is changed using the editor 70, the displayed waveforms may also change. This is illustrated in FIG. 8 when the property "pulse type" is about to be changed.

When the application is complete, the application container object is serialized and saved to storage. As indicated above, this serialized form of the application program may be restarted in another virtual Java™ machine such as the MRI system described above and reconstituted into an object-oriented application program ready for execution.

One advantage of the serialized configuration of the stored application program is that it can efficiently be downloaded to clinical MRI systems from remote sites. This may be done through direct serial connection using a private Intranet or a public telephone system, or it may be done through the Internet public system, satellite links, or various network connections. In any case, the transfer of the application program is a serialized object stream which carries the class name of each object, or component, as well as that component's instance data which is described by attribute name, type, and value. Also transferred is the relationships between components which allows a graph of the components in the application program to be collected in the serial stream received at the MRI system and then recreated, or reconstituted, on the MRI system. The serialization mechanism follows all relationships between objects. Each object, or component in the graph is only serialized once. Should a component be referenced more than one time, the serialization process recognizes the repeat and inserts a reference to the previous occurrence in the graph. This prevents duplication of objects and reduces the magnitude of the download task.

The serialization process also eliminates the need for downloading byte code. This presumes that any MRI system that receives a downloaded application program has a library which stores the byte code for all components contained in the application program. Updates to clinical systems may, therefore, include both the downloading of new applications as well as the downloading of any necessary new components for the MRI system library.

Of course, the serialization process also enables applications to be uploaded from clinical MRI systems. This enables applications and/or components developed at clinical research systems to be uploaded to the MRI system manufacturer for review and analysis.

The application development system can also be operated in a simulation mode to try out the application program before an actual scan is performed on the MRI system hardware. This simulation capability is facilitated by the fact that the application program will run on any Java™ virtual machine with a suitable component library. It is also facilitated by the fact that the user interface is a component of the application, such that the simulation uses the same interface and displays the same information as when running on an MRI system. Simulation environment is a mode of operation of the application development system which allows a developer to test and debug his/her application in a near-scanner like environment. The Java application loaded in the component assembler collection can be first saved and then simulation may be started. During simulation, the servers are in "simulation mode" and thus certain hardware interfaces are emulated or non-functional. Typically raw data is injected into the server imaging chain to be processed as it would if received by the transceiver.

During application simulation, the developer will have the opportunity to do certain levels of message tracing and component debug. The developer is provided with several levels of component message tracing, which can be set dynamically during application simulation. The developer may also invoke several levels of debug. During component and application development, the developer can set a "debug=TRUE" property in each component in order to access custom debug behavior for that component. Or, there may be several levels of debug for a property, with "0" being none or "debug off". For example, the sequencing component of the sequence description may provide for single stepping of the slice and phase encoding looping. Any custom user interfaces required for a given component are provided by that component in debug mode.

There may also be one or more simulation user interfaces which can be accessed during simulation to provide access to more global operations, such as observing the internal behavior of a specific server, inter-server tag communications or perhaps observing detailed behavior of a specific server, including tags and agent behavior.

The invention claimed is:

1. An application development computer system for a medical imaging system, which comprises:

a component library for storing components written in an object-oriented programming language, wherein one or more component includes at least one connection point for receiving an input or providing an output and wherein each component provides a predefined function; and a graphic building area, wherein a user selectively moves components from the component library to the graphic building area and selectively graphically links at least one connection point from a selected component to a connection point of another of the selected components, the graphical link providing a software reference to each of the selected components to define an executable application, the graphical links being modifiable during operation to provide an executable application segment;

a component for serializing and downloading the executable application to the medical imaging system; and a component for serializing and downloading the executable application segment to the medical imaging system to modify the executable application in real time.

2. The system as recited in claim 1 in which the components are displayed as icons.

3. The system as recited in claim 2 which includes a property display which enables a user to verify the properties of the component icon by selecting the icon with an input device.

4. The system as recited in claim 3 in which the connection points of the components are displayed as icons linked to the components.

5. The system as recited in claim 1 in which the object-oriented programming language is Java™ and the medical imaging system is programmed to translate the executable application to at least one of a C or a C++ program for real-time execution.

6. The system as recited in claim 1 in which the components include a serialization component, the serialization component allowing a user to transfer code from the application development system to an application server.

7. The system as recited in claim 1 wherein the component library further comprises an external communications link for receiving components and applications transmitted from an external central processing unit.

8. The system as recited in claim 7, wherein the external communications link comprises an internet link.

9. The system as recited in claim 7 wherein the external communications link comprises an ethernet link.

10. The application development system as defined in claim 1, wherein the executable application segments provide a data processing pipeline.

11. The application development system as recited in claim 10, wherein the data processing pipeline comprises a fast Fourier transform and the executable application segment is selectively modifiable to provide at least one of an array of magnitude data and an array of phase data to a data processor.

12. A magnetic resonance imaging system, which comprises:
a magnet assembly including a polarizing magnet, a gradient coil assembly, and an RF coil;
at least one application server coupled to the RF coil and to the gradient coil assembly to drive the gradient coils and the RF coil to perform a magnetic resonance imaging scan, to acquire imaging data from the scan, and to process the acquired image data from the scan;
a memory for storing a library comprising components written in an object-oriented programming language;
a workstation coupled to the application server for downloading program elements to a pulse sequence server to drive the RF coil and the gradient coil assembly, the workstation including a graphical application development system for graphically assembling object-oriented components to provide a waveform of control pulses for driving each of the gradient coils and the RF coil having a display, an input device and a processor programmed to perform application development functions, the application development program including:
a graphical building area for displaying icons representing components in the component library and responsive to directions from a user entered through the input device to selectively graphically link icons to assemble the components into executable medical imaging applications and to selectively modify the links during operation of the medical imaging applications to produce serialized and download executable program segments which modify the medical image application in real time.

13. The system as recited in claim 12 in which the icons in the graphical building area include a property area, the property area being activated by the input device to display properties associated with the selected component in the properties area.

14. The system as recited in claim 13 in which the application development program also includes a property editor which enables a user to input data through the input device to change property values of a component.

15. The magnetic resonance imaging system as recited in claim 12, wherein the library of components includes a program component for downloading an executable application segment.

16. The magnetic resonance imaging system as recited in claim 12, wherein the executable application segment provides a data processing pipeline.

17. The magnetic resonance imaging system as recited in claim 16, wherein the data processing pipeline comprises a fast Fourier transform and the executable application segment is selectively modifiable to provide at least one of an array of magnitude data and an array of phase data to a data processor.

* * * * *

UNITED STATES PATENT AND TRADEMARK OFFICE
CERTIFICATE OF CORRECTION

PATENT NO. : 7,020,868 B2  Page 1 of 1
APPLICATION NO. : 09/839055
DATED : March 28, 2006
INVENTOR(S) : Debbins et al.

It is certified that error appears in the above-identified patent and that said Letters Patent is hereby corrected as shown below:

Col. 16, lines 12 & 13 (Claim 12), delete "medical imaging applications to produce serialized and download executable program segments" and substitute therefore -- medical imaging applications to produce, serialize, and download executable program segments --.

Signed and Sealed this

Fourth Day of July, 2006

JON W. DUDAS
*Director of the United States Patent and Trademark Office*